(12) United States Patent
Lulo

(10) Patent No.: US 6,183,491 B1
(45) Date of Patent: Feb. 6, 2001

(54) EMBOLIC COIL DEPLOYMENT SYSTEM WITH IMPROVED EMBOLIC COIL

(75) Inventor: Robert Lulo, Pembroke Pines, FL (US)

(73) Assignee: Cordis Corporation, Miami Lakes, FL (US)

(*) Notice: Under 35 U.S.C. 154(b), the term of this patent shall be extended for 0 days.

(21) Appl. No.: 09/256,161

(22) Filed: Feb. 22, 1999

Related U.S. Application Data

(60) Provisional application No. 60/077,455, filed on Mar. 10, 1998.

(51) Int. Cl.[7] .................................................... A61M 29/00
(52) U.S. Cl. ............................................ 606/191; 606/195
(58) Field of Search .................................. 606/200, 198, 606/190–191, 108, 194–195; 604/99, 96, 282; 623/11–12, 1

(56) References Cited

U.S. PATENT DOCUMENTS

| | | |
|---|---|---|
| 2,853,070 | 9/1958 | Julliard . |
| 3,334,629 | 8/1967 | Cohn . |
| 3,353,718 | 11/1967 | McLay . |
| 4,512,338 | 4/1985 | Balko et al. . |
| 4,743,230 | 5/1988 | Nordquest . |
| 4,832,692 | 5/1989 | Box et al. . |
| 4,919,121 | 4/1990 | Rydell et al. . |
| 4,994,069 | 2/1991 | Ritchart et al. . |
| 5,108,407 | 4/1992 | Geremia et al. . |
| 5,122,136 | 6/1992 | Guglielmi et al. . |
| 5,137,514 | 8/1992 | Ryan . |
| 5,167,624 | 12/1992 | Butler et al. . |
| 5,168,757 | 12/1992 | Rabenau et al. . |
| 5,217,484 | 6/1993 | Marks . |
| 5,234,437 | 8/1993 | Sepetka . |
| 5,250,071 | 10/1993 | Palermo . |
| 5,261,916 | 11/1993 | Engelson . |

(List continued on next page.)

FOREIGN PATENT DOCUMENTS

| | | |
|---|---|---|
| 0 717 969 | 6/1996 | (EP) . |
| 0941700 * | 9/1999 | (EP) .............................. A61B/17/12 |
| 0941703 * | 9/1999 | (EP) .............................. A61B/17/12 |
| 0941704 * | 9/1999 | (EP) .............................. A61B/17/12 |
| WO 98/02100 | 1/1998 | (WO) . |

OTHER PUBLICATIONS

Brochure entitled, "Guglielmi Detachable Coils," by Boston Scientific.
Label of IDC–18 Interlocking Detachable Coil by Target Therapeutics, Inc.
Brochure entitled, "Detachable Coil System," by Cook.
Brochure entitled, "Basix25™ Inflation Device," by Merit Medical Systems, Inc.
Brochure entitled, "Monarch AP® Inflation Device," by Merit Medical Systems, Inc.
Label of B. Braun Inflation Device Kit by B. Braun Medical Inc.

*Primary Examiner*—Michael Buiz
*Assistant Examiner*—Jonathan D. Goldberg
(74) *Attorney, Agent, or Firm*—Henry W. Collins

(57) ABSTRACT

A medical device for placing an embolic coil at a preselected location within a vessel comprising a positioning catheter having a distal tip for retaining the embolic coil which when pressurized with a fluid expands outwardly to release the coil at the preselected position and including an embolic coil having a relatively flexible proximal portion which resists stretching.

17 Claims, 2 Drawing Sheets

U.S. PATENT DOCUMENTS

| | | |
|---|---|---|
| 5,263,964 | 11/1993 | Purdy . |
| 5,304,195 | 4/1994 | Twyford, Jr. et al. . |
| 5,312,415 | 5/1994 | Palermo . |
| 5,334,210 | 8/1994 | Gianturco . |
| 5,336,183 | 8/1994 | Greelis et al. . |
| 5,342,304 | 8/1994 | Tacklind et al. . |
| 5,350,397 * | 9/1994 | Palmero et al. ............... 606/200 |
| 5,382,259 | 1/1995 | Phelps et al. . |
| 5,417,708 * | 5/1995 | Hall et al. ............... 606/200 |
| 5,443,478 | 8/1995 | Purdy . |
| 5,470,317 | 11/1995 | Cananzey et al. . |
| 5,578,074 | 11/1996 | Mirigian . |
| 5,582,619 | 12/1996 | Ken . |
| 5,601,600 | 2/1997 | Ton . |
| 5,603,698 * | 2/1997 | Roberts et al. ............... 606/108 |
| 5,609,608 | 3/1997 | Benett et al. . |
| 5,624,461 * | 4/1997 | Mariant ............... 606/191 |
| 5,639,277 * | 6/1997 | Mariant et al. ............... 606/191 |
| 5,647,847 | 7/1997 | Lafontaine et al. . |
| 5,853,418 | 12/1998 | Ken et al. . |
| 6,063,100 * | 5/2000 | Diaz et al. ............... 606/191 |
| 6,068,644 * | 5/2000 | Lulo et al. ............... 606/191 |

* cited by examiner

EMBOLIC COIL DEPLOYMENT SYSTEM WITH IMPROVED EMBOLIC COIL

This application claims benefit to provisional application 60/077455 filed Mar. 10, 1998.

BACKGROUND OF THE INVENTION

1. Field of the Invention

The present invention relates to a medical device for placing an embolic coil at a preselected location within a vessel of the human body, and more particularly, relates to a catheter having a distal tip for retaining the embolic coil in order to transport the coil to a preselected position within the vessel and a control mechanism for releasing the embolic coil at the preselected position.

2. Description of the Prior Art

For many years flexible catheters have been used to place various devices-within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407, entitled "Method And Apparatus For Placement Of An Embolic Coil"; U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils to preselected position within vessel of the human body in order to treat aneurysms or alternatively to occlude the blood vessel at the particular location.

Coils which are placed in vessels may take the form of helically wound coils, or alternatively, may be random wound coils, coils wound within other coils or many other such coil configurations. Examples of various coil configurations are disclosed in U.S. Pat. No. 5,334,210, entitled, "Vascular Occlusion Assembly; U.S. Pat. No. 5,382,259, entitled, "Vasoocclusion Coil With Attached Tubular Woven Or Braided Fibrous Coverings." Embolic coils are generally formed of a radiopaque metallic materials, such as platinum, gold, tungsten or alloys of these metals. Often times several coils are placed at a given location in order to occlude the flow of blood through the vessel by promoting thrombus formation at the particular location.

In the past, the proximal end of embolic coils have been placed within the distal end of the catheter and when the distal end of the catheter is properly positioned the coil may then be pushed out of the end of the catheter with, for example a guidewire, to release the coil at the desired location. This procedure of placement of the embolic coil is conducted under fluoroscopic visualization such that the movement of the coil through the vasculature of the body may be monitored and the coil may be placed in the desired location. With these placements systems there is very little control over the exact placement of the coil since the coil may be ejected to a position some distance beyond the end of the catheter. As is apparent, with these latter systems, when the coil has been released from the catheter it is difficult, if not impossible, to retrieve the coil or to reposition the coil.

Numerous procedures have been developed to enable more accurate positioning of coils within a vessel. Still another such procedure involves the use of a glue or solder for attaching the embolic coil to a guidewire which, is in turn, placed within a flexible catheter for positioning the coil within the vessel at a preselected position. Once the coil is at the desired position, the coil is restrained by the catheter and the guidewire is pulled from the proximal end of the catheter to thereby cause the coil to be detached from the guidewire and released from the catheter system. Such a coil positioning system is disclosed in U.S. Pat. No. 5,263,964, entitled, "Coaxial Traction Detachment Apparatus And Method."

Another coil positioning system utilizes a catheter having a socket at the distal end of the catheter for retaining a ball which is bonded to the proximal end of the coil. The ball, which is larger in diameter than the outside diameter of the coil, is placed in a socket within the lumen at the distal end of the catheter and the catheter is then moved into a vessel in order to place the coil at a desired position. Once the position is reached, a pusher wire with a piston at the end thereof is pushed distally from the proximal end of the catheter to thereby push the ball out of the socket in order to thereby release the coil at the desired position. Such a system is disclosed in U.S. Pat. No. 5,350,397, entitled, "Axially Detachable Embolic Coil Assembly." One problem with this type of coil placement system which utilizes a pusher wire which extends through the entire length of the catheter and which is sufficiently stiff to push an attachment ball out of engagement with the socket at the distal end of the catheter is that the pusher wire inherently causes the catheter to be too stiff with the result that it is very difficult to guide the catheter through the vasculature of the body.

Another method for placing an embolic coil is that of utilizing a heat releasable adhesive bond for retaining the coil at the distal end of the catheter. One such system uses laser energy which is transmitted through a fiber optic cable in order to apply heat to the adhesive bond in order to release the coil from the end of the catheter. Such a method is disclosed in U.S. Pat. No. 5,108,407, entitled, "Method And Apparatus For Placement Of An Embolic Coil." Such a system also suffers from the problem of having a separate element which extends throughout the length of the catheter with the resulting stiffness of the catheter.

Still another method for placing an embolic coil is disclosed in co-pending U.S. patent application Ser. No. 09/177,848, entitled "Embolic Coil Hydraulic Deployment System," filed on Oct. 21, 1998 and assigned to the same assignee as the present patent application. This patent application discloses the use of fluid pressure which is applied to the distal tip of the catheter for expanding the lumen in order to release the embolic coil.

Various embolic coil designs have been proposed for use with coil deployment systems such as the stretch resistant vaso-occlusive coil disclosed in U.S. Pat. No. 5,853,418, entitled "Stretch Resistant Vaso-occlusive Coils," which discloses a helically wound coil having a polymeric stretch resisting member extending through the lumen of the coil and fixedly attached to both the distal end and the proximal end of the coil. While the stretch resisting member prevents the coil from being stretched during use, this member which extends throughout the length of the coil tends to significantly reduce the flexibility of the coil. This reduced flexibility may present problems because in order to place vaso-occlusive coils into a desired location and have the coil property employ it is very important that the coil be very flexible.

SUMMARY OF THE INVENTION

The present invention is directed toward a vascular occlusive coil deployment system for use in placing an embolic coil at a preselected site within a vessel which includes an elongated, flexible catheter having a distal tip for retaining the coil so that the coil may be moved to the preselected position within the vessel. The catheter has a lumen which extends therethrough the length of the catheter and also includes a distal end which is formed of a material having a durometer such that when a fluid pressure of about 90 to 450 pounds per square inch (psi) is applied to the interior of the catheter, the walls of the distal tip expand outwardly, or radially, to thereby increase the lumen of the distal tip of the catheter. The proximal end of the embolic coil is placed into the lumen of the distal tip of the catheter and is retained by the distal tip of the catheter. A hydraulic injector, such as a syringe, is coupled to the proximal end of the catheter for applying a fluid pressure to the interior of the catheter. When the coil is placed at a desired position within a vessel, fluid pressure is then applied to the interior of the catheter by the hydraulic injector to thereby cause the walls of the distal tip to expand outwardly to thereby release the coil for placement in the vessel.

In order to prevent the proximal portion of the coil, which is held by the distal tip of the catheter, from stretching and unwinding, to thereby cause a premature release of the coil, the proximal portion of the coil is modified in a manner so as to "lock" adjacent turns of the coil together to thereby prevent such stretching or unwinding. The coil preferably takes the form of a tightly wound helical coil having a proximal end, a distal end and a lumen extending therethrough. The coil includes a seal plug which is disposed in fluid-tight engagement within the coil lumen at the proximal end of the coil. In addition, the coil includes a support wire which extends along the central axis of the coil lumen for a length substantially less than the length of the coil and in which one end of the support wire is fixedly attached to the seal plug and the other end of the support wire is fixedly attached to at least one of the turns of the coil at a point substantially remote from the distal end of the coil. With this design, all of the turns of the coil between the proximal end of the coil and the point on the coil where the support wire is attached are tightly secured to each other thereby preventing this proximal portion of the coil from stretching or unwinding while still being very flexible.

In accordance with another aspect of the present invention, the flexible catheter is comprised of a proximal section and a relatively short distal section. The proximal section is formed of a material which is sufficiently flexible to be passed through the vasculature of the human body and is of a durometer which essentially resists outward expansion when a fluid pressure on the order of about 90 to 450 psi is applied to the interior of the catheter. The distal section of the catheter is formed of a material which is also sufficiently flexible to be passed through the vasculature of the body, yet is of a durometer which is significantly lower than the durometer of the proximal section and exhibits the property of expanding outwardly, or radially, when such a fluid pressure is applied to the interior of the catheter to thereby permit the release of the embolic coil.

In accordance with still another aspect of the present invention, the distal section of the catheter has a durometer in a range of between about 25 D and 55 D.

In still another aspect of the present invention, the embolic coil is comprised of a helical coil having a proximal end, a distal end, and a lumen extending therethrough. A seal plug is disposed within the lumen of the proximal end of the coil in fluid-tight engagement. The proximal end of the coil is disposed in a fluid-tight engagement within the lumen of the distal section of the catheter and is retained by the lumen of the catheter for subsequent release.

In another aspect of the present invention, the hydraulic injector for applying a fluid pressure to the interior of the catheter takes the form of a syringe which is coupled to the proximal end of the catheter for, upon movement of the piston, creating a fluid pressure which is applied to the interior of the catheter to thereby cause the release of the embolic coil.

In accordance with another aspect of the present invention, the embolic coil may take the form of other types of implantable devices, such as a vascular filter.

In another aspect of the present invention, there is provided a method for placing an embolic coil with a selected site within a vessel of the body comprising the steps of advancing a catheter through the vasculature of the body to place an embolic coil which is retained within the lumen of the distal tip of the catheter to a preselected site, applying a fluid pressure to the interior of the catheter to thereby cause the distal tip of the catheter to expand radially outwardly to release the embolic coil at the preselected site, and withdrawing the catheter from the vasculature system.

With the coil design of the present invention the proximal portion of the coil is prevented from stretching or unwinding to thereby prevent the premature release of the coil from the catheter deployment system.

These aspects of the invention and the advantages thereof will be more clearly understood from the following description and drawings of a preferred embodiment of the present invention:

DESCRIPTION OF A PREFERRED EMBODIMENT

Figure 1:
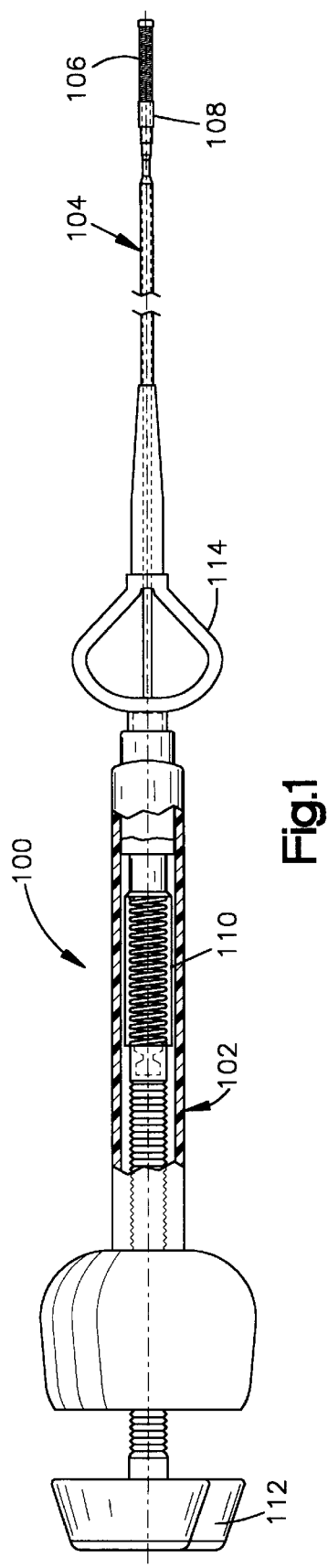
FIG. 1 is an enlarged, partially sectioned view of the hydraulic vascular occlusive coil deployment system of the present invention.

FIG. 1 generally illustrates the vascular occlusive coil deployment system 100 which is comprised of a hydraulic injector or syringe 102, coupled to the proximal end of a catheter 104. An embolic coil 106 is disposed within the lumen of the distal end 108 of the catheter. The proximal end of the coil 106 is tightly held within the lumen of the distal section 108 of the catheter 104 until the deployment system is activated for release of the coil. As may be seen, the syringe 102 includes a threaded piston 110 which is controlled by a handle 112 for infusing fluid into the interior of the catheter 104. Also as illustrated, the catheter 104 includes a winged hub 114 which aids in the insertion of the is catheter into the vascular system of the body.

Figure 2:
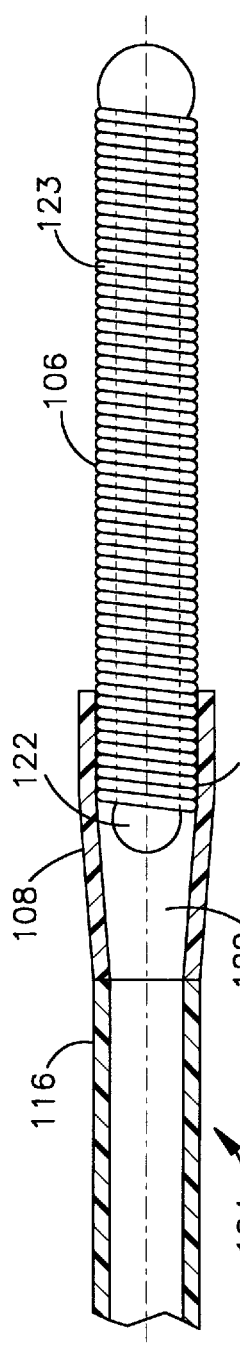
FIG. 2 is an enlarged partially sectioned view showing the distal end of the coil deployment system prior to deployment of the coil.

FIG. 2 illustrates in more detail the distal end of the catheter 104. The catheter 104 includes a proximal section 116 and the distal section 108. The proximal section 118 of the embolic coil 106 is disposed within the distal section 108 of the catheter and is tightly held within the lumen 120 of this distal section 108 prior to release of the coil. As may be appreciated, FIG. 2 illustrates the vascular occlusive coil deployment system prior to activation of the piston of the syringe and prior to release of the coil.

The embolic coil 106 may take various forms and configurations and may even take the form of a randomly wound coil, however, with the helical wound coil as illustrated in FIG. 2, the coil is provided with a weld bead or seal plug 122 which is disposed in a lumen 123 which lumen extends throughout the length of the coil 106. The seal plug 122 serves to prevent the flow of fluid through the lumen of the coil 106 so that when the coil 106 is placed in fluid-tight engagement with the lumen 120 the coil serves to provide a fluid-tight seal at the distal end of the catheter 104. A liquid silicone material 130a is injected into the space surrounding the support wire 130 to fill the proximal portion of the lumen of the coil. The silicone material is then cured to seal the proximal end of the coil to prevent fluid leakage through the turns of the coil. The cured remains flexible with the result that the proximal end of the coil remains flexible.

Preferably, the proximal section 116 and the distal section 108 of the catheter 104 are formed of materials having different durometers. The proximal section 116 is preferably formed of Pebax material having a durometer in a range of about 62 D to 75 D. The proximal section is sufficiently flexible to transverse the vasculature of the human body, but is sufficiently rigid such that when a fluid pressure of approximately 90 to 450 psi is applied to the interior of this section of the catheter there is very little, if any, radial expansion of the walls of this section. On the other hand, the distal section 108 of the catheter is preferably formed of polymer material with a relatively low durometer which, exhibits the characteristic that when a fluid pressure of approximately 90 to 450 psi is applied to the interior of the catheter the walls of the distal section 108 expand radially, somewhat similar to the action of a balloon inflating, to thereby release the proximal end 118 of the coil 106. As may be appreciated, there are numerous materials which could be used to fabricate the proximal section 116 and distal section 108 of the catheter 104, however, the distal section 108 is preferably formed from a block copolymer such as Pebax having a durometer of between 25 D and 55 D with a durometer of 40 D being the preferred durometer.

Figure 3:
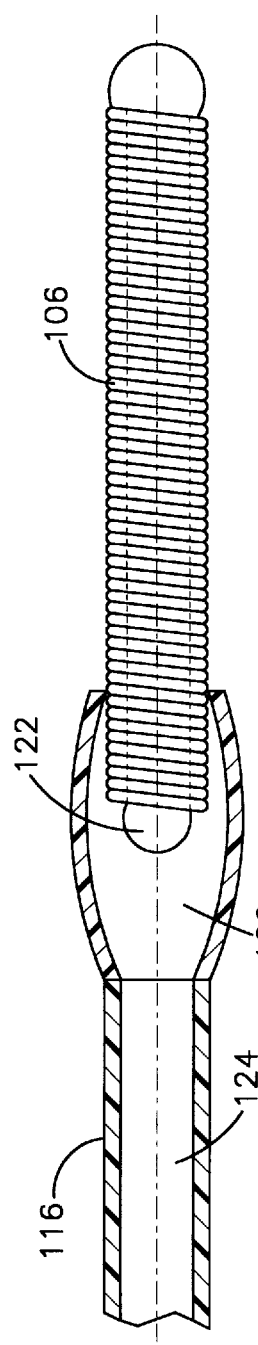
FIGS. 3 and 4 illustrate the sequential steps in the radial expansion of the distal tip of the coil deployment system as the embolic coil is released.
Figure 4:
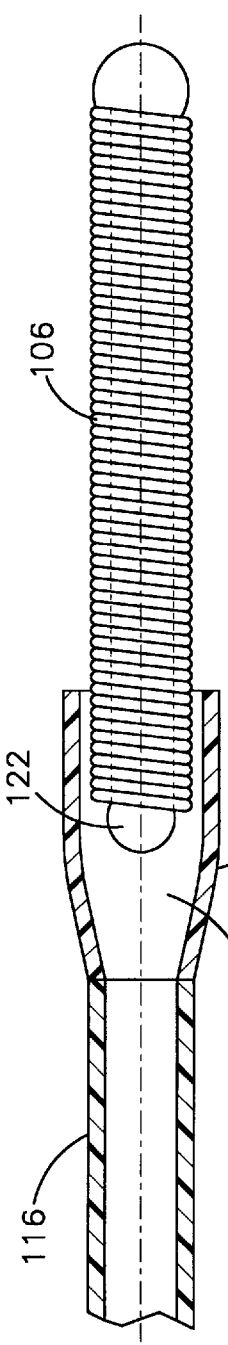

FIGS. 3 and 4 generally illustrate the coil release mechanism in action for the vascular occlusive catheter deployment system. More particularly, as shown in FIG. 3, when a hydraulic pressure is applied to the interior 124 of the catheter 104 the relatively low durometer distal section 108 of the catheter begins to expand radially, much as a balloon expands during the process of inflation. As the distal section 108 continues to expand radially there comes a point as illustrated in FIG. 4 in which the coil 106 becomes disengaged from the lumen of the distal section 108 and the coil is then released from the catheter and is deployed at that location within the vessel.

Figure 5:
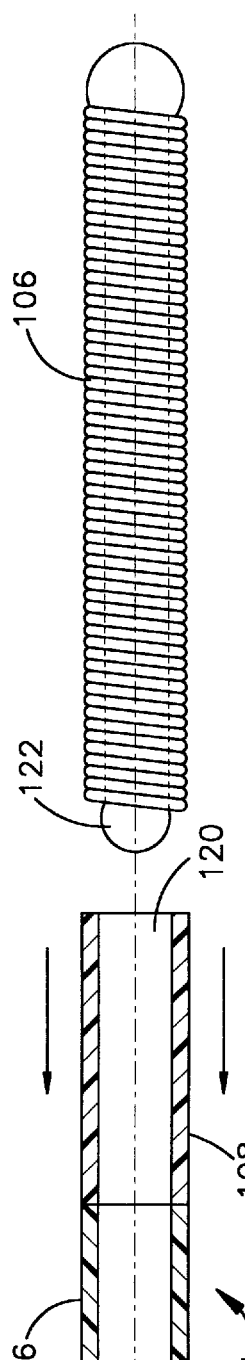
FIG. 5 illustrates the distal tip of the coil deployment system after release of the embolic coil; and, FIG. 6 is a partially sectioned view showing the coil retaining structure of the present invention.

As illustrated in FIG. 5, when the coil 106 has been released from the catheter 104 the catheter may then be withdrawn leaving the coil positioned at the desired site.

Figure 6:
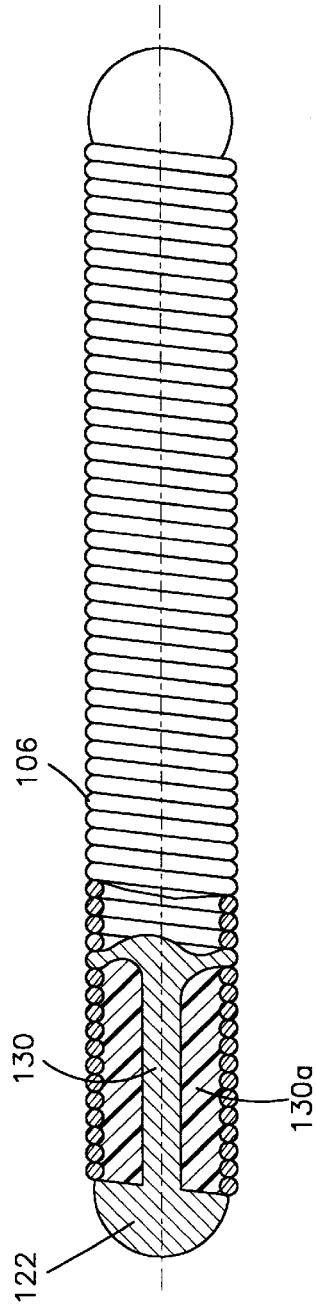

As illustrated in FIG. 6, the vaso-occlusion or embolic coil 106 is formed by winding a platinum alloy wire into a tightly wound helical configuration. The diameter of the wire is generally in the range of about 0.0015 inches to 0.008 inches. The outside diameter of the coil 106 is preferably in a range of about 0.006 inches to 0.055 inches. While the particular embolic coil 106 illustrated in FIG. 6 is shown as being a straight coil it should be appreciated that embolic coils take the form of various configurations and may take the form of a helix, a random shape configuration or even a coil within a coil configuration.

With the embodiment of the coil deployment system disclosed in this application it may be noted that the first several turns on the proximal end of the embolic coil 106 are retained or held by the distal tip of the catheter as the coil is moved in position. Often times it is necessary to move a coil to a certain position within the vasculature and then to withdraw the coil back to a more proximal position within the vasculature. During the movement of a coil through the vasculature, particularly when the coil is withdrawn to a more proximal position within the vasculature, it is possible to stretch or unwind the turns of the coil. If the turns of the coil which are held by the distal tip of the deployment catheter are stretched or unwound the result is that the outside diameter of the coil decreases with the result that the coil may be prematurely released from the deployment system.

In order to prevent the proximal portion of the coil 106 from stretching or unwinding, a platinum support wire 130 is welded to the proximal sealing plug 122. The other end of the platinum support wire 130 is bonded by welding to one of the turns of the coil at a position relatively close to the proximal end of the catheter. Preferably, the embolic coil is of a length in a range of about 1.5 centimeters to 30 centimeters. The length of the support wire is of a length in the range of about 0.5 millimeters to about 4 millimeters and the diameter of the support wire is between about 0.0007 and 0.002 inches. With this arrangement, the overall flexibility of the embolic coil 106 is maintained while providing a means for preventing the stretching or unwinding of the gripped portion of the coil. As may be appreciated, the proximal sealing plug may take the form of a welded bead which is formed at the end of the support wire 130. Also, the support wire may be attached to the weld bead and to the turns of the coil by soldering, welding, or by the use of an adhesive. The support wire could be formed of various different materials including polymers or composites. A liquid silicone material 130a is injected into the space surrounding the support wire 130 to fill the proximal portion of the lumen of the coil. The silicone material is then cured to seal the proximal end of the coil to prevent fluid leakage through the turns of the coil.

With the vascular occlusive coil deployment system of the present invention it is possible to place an embolic coil very precisely at a desired location within a vessel. Once the coil has been placed in that location by use of the catheter, the catheter may be activated by applying a hydraulic pressure to the interior of the catheter to thereby cause the catheter to release the coil and deposit the coil very accurately at the desired location.

As is apparent, there are numerous modifications of the preferred embodiment described above which will be readily apparent to one skilled in the art, such as many variations and modifications of the coil including numerous coil winding configurations, or alternatively other types of implant devices, such as a vascular filter. Also, there are obviously variations of the syringe arrangement for applying a fluid pressure to the interior of the catheter, including many other fluid pressure generating systems for increasing the pressure within the interior of a catheter in order to cause the distal section of the catheter to expand. These modifications would be apparent to those having ordinary skill in the art to which this invention relates and are intended to be within the scope of the claims which follow.

That which is claimed is:

1. A vaso-occlusive coil deployment system for use in placing a coil at a preselected site within a vessel comprising:

an elongated flexible catheter having a lumen extending therethrough and having a proximal section and a distal section, said distal section of the catheter being formed of a material having a durometer which exhibits the characteristic that when a fluid pressure is applied to the interior of the catheter the walls of the distal section of the catheter expand outwardly;

a syringe coupled to the proximal section of the catheter for applying a fluid pressure to the interior of the catheter to thereby cause the distal section of the catheter to expand outwardly; and, an embolic coil being disposed in fluid-tight engagement within the lumen of the distal section of the catheter, said coil comprising a tightly wound helical coil having a proximal end, a distal end and an embolic coil lumen extending therethrough, a seal plug is disposed in fluid-tight engagement within the embolic coil lumen at the proximal end of the embolic coil, a support wire extends along the central axis of the embolic coil lumen for a length substantially less than the length of the coil, one end of said support wire being fixedly attached to the seal plug and the other end of the support wire being fixedly attached to the embolic coil at a point on an embolic coil lumen wall at a position substantially remote from the distal end of the embolic coil.

2. A vaso-occlusive coil deployment system as defined in claim 1, wherein the length of the embolic coil is in a range of about 1.5 to 30 centimeters and the length of the support wire is in a range of about 0.5 to 4 millimeters.

3. A vaso-occlusive coil deployment system as defined in Claim 1, wherein said proximal section of said catheter is formed of a material which is sufficiently flexible to be passed through the vasculature of the body and is formed of a material which exhibits the characteristic of having substantially no radial expansion when a fluid pressure of about 90 to 450 psi is applied to the interior of the catheter, the distal tip is formed of a material which is also sufficiently flexible to be passed through the vasculature of the body and is of a durometer which is substantially lower than the durometer of the proximal section.

4. A vaso-occlusive coil deployment system as defined in claim 3, wherein the distal tip of the catheter is formed of a polymer having a durometer in a range of between about 25 D and 55 D.

5. A vaso-occlusive coil deployment system as defined in claim 3, wherein the distal tip of the catheter has a durometer of about 40 D.

6. A vaso-occlusive coil deployment system as defined in claim 4, wherein said proximal section of said catheter is formed of a polymer having a durometer in a range of 62 D to 75 D.

7. A vaso-occlusive coil deployment system for use in placing a coil at a preselected site within a vessel comprising:

an elongated flexible catheter having a lumen extending therethrough and having a proximal section and a distal section, said distal section of the catheter being formed of a material having a durometer which exhibits the characteristic that when a fluid pressure of about 90 to 450 psi applied to the interior of the catheter the walls of the distal section of the catheter expand outwardly;

a piston coupled to the proximal section of the catheter for applying a fluid pressure to the interior of the catheter to thereby cause the distal section of the catheter to expand outwardly to thereby release the embolic coil; and, an embolic the embolic coil being disposed in fluid-tight engagement within the lumen of the distal section of the catheter, said coil comprising a tightly wound helical coil having a proximal end, a distal end and an embolic coil lumen extending therethrough, a seal plug is disposed in fluid-tight engagement within the embolic coil lumen at the proximal end of the embolic coil, a support wire extends along the central axis of the embolic coil lumen for a length substantially less than the length of the embolic coil, one end of said support wire being fixedly attached to the seal plug and the other end of the support wire being fixedly attached to the coil at a point on the lumen wall at a position substantially remote from the distal end of the coil.

8. A vaso-occlusive coil deployment system as defined in claim 7, wherein the length of the embolic coil is in a range of about 1.5 to 30 centimeters and the length of the support wire is in a range of about 0.5 to 4 millimeters.

9. A vaso-occlusive coil deployment system as defined in claim 8, wherein said proximal section of said catheter is formed of a material which is sufficiently flexible to be passed through the vasculature of the body and is formed of a material which exhibits the characteristic of having substantially no radial expansion when a fluid pressure of about 90 to 450 psi is applied to the interior of the catheter, a distal tip is formed of a material which is also sufficiently flexible to be passed through the vasculature of the body and is of a durometer which is substantially lower than the durometer of the proximal section.

10. A vaso-occlusive coil deployment system as defined in claim 9, wherein the distal tip of the catheter is formed of a polymer having a durometer in a range of between about 25 D and 55 D.

11. A vaso-occlusive coil deployment system as defined in claim 9, wherein the distal tip of the catheter has a durometer of about 40D.

12. A vaso-occlusive coil deployment system as defined in claim 10, wherein said proximal section of said catheter is formed of a polymer having a durometer in a range of about 62 D to 75 D.

13. A vaso-occlusive coil deployment system for use in placing a coil at a preselected site within a vessel comprising:

an elongated flexible catheter having a lumen extending therethrough and having a proximal section and a distal section, said distal section of the catheter being formed of a material having a durometer which exhibits the characteristic that when a fluid pressure of about 90 to 450 psi applied to the interior of the catheter the walls of the distal section of the catheter expand outwardly;

a fluid pressure generating device coupled to the proximal section of the catheter for applying a fluid pressure to the interior of the catheter to thereby cause the distal section of the catheter to expand outwardly; and, an embolic coil being disposed in fluid-tight engagement within the lumen of the distal section of the catheter, said coil comprising a tightly wound helical coil having a proximal end, a distal end and an embolic coil lumen extending therethrough, a seal plug is disposed in fluid-tight engagement within the embolic coil lumen at the proximal end of the embolic coil, a support wire extends along the central axis of the embolic coil lumen for a length substantially less than the length of the embolic coil, one end of said support wire being fixedly attached to the seal plug and the other end of the support wire being fixedly attached to the coil at a point on an embolic coil lumen wall at a position substantially remote from the distal end of the embolic coil.

14. A vaso-occlusive coil deployment system as defined in claim 13, wherein the length of the embolic coil is in a range of about 1.5 to 30 centimeters and the length of the support wire is in a range of about 0.5 to 4 millimeters.

15. A vaso-occlusive coil deployment system as defined in claim 14, wherein said proximal section of said catheter is formed of a material which is sufficiently flexible to be passed through the vasculature of the body and is formed of a material which exhibits the characteristic of having substantially no radial expansion when a fluid pressure of about 90 to 450 psi is applied to the interior of the catheter, a distal tip is formed of a material which is also sufficiently flexible to be passed through the vasculature of the body and is of a durometer which is substantially lower than the durometer of the proximal section.

16. A vaso-occlusive coil deployment system as defined in claim 15, wherein the distal tip of the catheter is formed of a polymer having a durometer in a range of between about 25 D and 55 D.

17. A vaso-occlusive coil deployment system as defined in claim 15, wherein the distal tip of the catheter has a durometer of about 40 D.

* * * * *